United States Patent
Hearn et al.

(10) Patent No.: US 6,532,064 B1
(45) Date of Patent: Mar. 11, 2003

(54) AUTOMATIC INSPECTION APPARATUS AND METHOD FOR SIMULTANEOUS DETECTION OF ANOMALIES IN A 3-DIMENSIONAL TRANSLUCENT OBJECT

(75) Inventors: Paul M. Hearn, Newfoundland (CA); Ernest M. Reimer, Newfoundland (CA)

(73) Assignee: Baader-Canpolar Inc. (CA)

( * ) Notice: Subject to any disclaimer, the term of this patent is extended or adjusted under 35 U.S.C. 154(b) by 0 days.

(21) Appl. No.: 09/977,695

(22) Filed: Oct. 16, 2001

(51) Int. Cl.[7] ............................................. G01N 21/00
(52) U.S. Cl. ................ 356/237.1; 356/239.4; 356/239.1
(58) Field of Search ............. 356/237.1–237.6, 356/239.1, 239.4–239.8, 240.1, 53; 250/223 B, 225, 262, 572

(56) References Cited

U.S. PATENT DOCUMENTS

| | | | |
|---|---|---|---|
| 4,585,315 A | | 4/1986 | Sincerbox et al. .......... 350/525 |
| 4,691,231 A | * | 9/1987 | Fitzmorris et al. ........ 356/240.1 |
| 4,978,225 A | * | 12/1990 | Reimer ..................... 356/239.1 |
| 5,216,481 A | * | 6/1993 | Minato .................... 356/240.1 |
| 5,426,509 A | * | 6/1995 | Peplinski ................. 356/239.1 |
| 5,493,123 A | | 2/1996 | Knollenberg et al. ....... 250/372 |
| 5,845,002 A | | 12/1998 | Heck et al. ................ 382/110 |
| 5,898,488 A | * | 4/1999 | Kuhl ........................... 356/53 |
| 6,049,379 A | | 4/2000 | Lucas ...................... 356/240.1 |
| 6,067,155 A | * | 5/2000 | Ringlien ................. 356/240.1 |
| 6,304,323 B1 | * | 10/2001 | Ishikura et al. .......... 356/239.4 |

FOREIGN PATENT DOCUMENTS

| US | WO 96/14169 | 9/1995 | ..................... 5/21 |
|---|---|---|---|
| US | WO 98/20327 | 11/1997 | ................... 21/88 |

OTHER PUBLICATIONS

Patent Abstracts of Japan—NEC Corporation, Nov. 24, 1989 "Defect Inspecting Device".
Patent Abstracts of Japan—Dainippon Printing Co. Ltd. Jan. 23, 1995 "Methods for Inspecting Defects of Lenticular Lens Sheet".
Patent Abstracts of Japan—Mar. 10, 1997 Dakku Engineering—Quality Inspection Device.

* cited by examiner

*Primary Examiner*—Frank G. Font
*Assistant Examiner*—Sang H. Nguyen
(74) *Attorney, Agent, or Firm*—McFadden, Fincham; Ian Fincham (57) ABSTRACT

The present invention relates to an automated inspection apparatus for detection of anomalies in a 3D translucent object, the apparatus having a scanhead assembly including an image processing unit and image capture device, a first and a second light source, and conveyor means, the improvement comprising a light block member positioned along a substantially common axis of the image capture device and a light source.

21 Claims, 5 Drawing Sheets

AUTOMATIC INSPECTION APPARATUS AND METHOD FOR SIMULTANEOUS DETECTION OF ANOMALIES IN A 3-DIMENSIONAL TRANSLUCENT OBJECT

FIELD OF INVENTION

The invention relates to an automated inspection apparatus and method for use in the optical inspection of 3-dimensional (3D) translucent objects such as fish, to simultaneously identify surface, embedded and semitransparent edge anomalies and distinguishing features.

BACKGROUND ART

Translucent objects, such as fish, often contain defects or conditions which lead to or cause contamination of the object. It is necessary to eliminate these, contaminated areas or objects and, as such, a reliable method for detecting these features or anomalies has been the subject matter of certain prior art.

Reliable detection of optical characteristics of a translucent object poses difficulties due to illumination, which is used during inspection, being either adsorbed by the object or scattered unevenly over the object. Conventional illumination can be too bright in certain areas or too dim in others. Another problem associated with detection of foreign objects is the creation of shadows or extreme brightness which results in an image capture device "stopping-up" or "stopping-down" the aperture to prevent under or overexposure.

Typical light sources range from conventional light fixtures to ultra violet spectrum. As an example, halogen lighting can be used to provide an overall light source for the inspection of an object such as a fish fillet. The use of UV is standard for the purposes of inspecting glass.

Surface, embedded and semi-transparent edge anomalies in translucent objects such as fish are characteristically only manifested under appropriate dark field or bright field illumination. As such, dark and bright field illumination are typically addressed individually due to light path propagation during compensation for individual manifestation characteristics of the anomalies.

For example, bright field lighting is a lighting technique which directs specular or diffuse reflections of light to the camera. Surface defects, such as blood and skin are detected with this technique. Dark field lighting is a lighting technique which directs back scattered light from the surface of an object to the camera. Embedded, anomalies, such as a parasite, and semi-transparent edge anomalies, such as transparent bones, in a fish fillet are detectable. with this technique. However, use of either technique presents known difficulties as summarized hereinafter. Changing light levels or the creation of geometrical shadows can distort accurate sensor detection.

Conventional methods used for anomaly detection for fish processing entail placing a fish on a light table having a surface illuminated. At least one lamp is used to illuminate the target area in bright field light. Operators visibly inspect a fish fillet to identify surface, embedded and semi-transparent edge anomalies.

Inherent to this method is visual fatigue, inconsistent visual perception by an operator and optical disparity between operators. Attempts have been made to overcome these difficulties by known art.

Examples of art that discuss several ways of properly illuminating and inspecting an object. include U.S. Pat. Nos. 4,585,315; 5,845,002; 6,022,124; 6,049,379; 5,493,123; international patents PCT/US95/11318 (equivalent to U.S. Pat. No. '002); PCT/US97/20058; Japanese patents 3165534A2; 8201222A2; and 11108637A2.

U.S. Pat. No. '315 discusses a bright field and dark field microscope illuminator with two axicon mirrors, a third plane mirror and shutters positioned in the paths of the light beams. Through use of the disclosed embodiments, simultaneous bright and dark field illumination or alternatively singularly bright or dark field illumination is achieved through the opening and closing of the appropriate shutters. However, the advantages of even illumination of a translucent object would technically obviate from detection of translucent or transparent anomalies that would manifest under variant light intensities. Simultaneous detection of surface, embedded and semitransparent edge anomalies is not possible with the use of only dark or bright field illumination.

U.S. Pat. No. '002 teaches a method of statistical evaluation of a translucent object by scanning graphic images of an object and processing incident light frequencies enabling a pixel by pixel analysis of topographic surface features of a fruit. A selected frequency, or combinations of frequencies, of light is directed at the fruit according to porosity of the peel. A computerized optical scanner having two light sources disposed at approximately 120 degrees from a vertical plane emit incident light towards an object, or to mirrors, to effectively scatter incident light within the fruit and cause the fruit to "glow". A frequency spectrum is selected based on maximum, minimum and standard deviation of the intensity of the entire pixel pattern constituting the image. Both hemispheres of a fruit are analyzed; an algorithm assists in eliminating portions of the graphic information that are not relevant (such as bright field illumination or reflected light sources), and which do not constitute "glow" from the fruit. Sharp transitions are evaluated by filtering the image and comparing aberrations pixel by pixel. International application WO 96/14169 is derived from U.S. Pat. No. '002. Application of the above methodology prohibits bright field illumination techniques that enable detection of transparent anomalies such as skin and bones embedded or on the surface of a fish fillet.

U.S. Pat. No. '124 discloses a ring-light source and reflective ring focusing element wherein LED's are strung in one or more circular rows and strobe (or pulse) light to ring reflectors provides uniform lighting of an object. Light emissions from the LED's approach the object at an angle oblique or perpendicular to the optical axis. The effective dark field illumination patterns are intended to minimize light from the illumination source from entering the camera. However, use of only a dark field technique during inspection of a translucent object, such as a fish, severely diminishes the manifestation of those anomalies, thus requiring bright field techniques.

U.S. Pat. No. '379 shows a method of scanning multiple images of a translucent object and applying brightness ratios to the scanned images for the detection of flaws in the target area. A glass bottle is disclosed wherein light intensity readings are analyzed based on an acceptable range of ratios determined by a target area and a control area. The allowable range is calculated by analyzing an object with known defects and an object that is known-to be non-defective. The disclosure notes that "blind spots" may arise during inspection for defects.

The techniques of U.S. Pat. No. '123 involves the use of ultra violet radiation during a predetermined inspection period of glass. Use of ultra violet radiation during the inspection of organic materials for consumption is not desirable.

International patent PCT/US97/20058 discloses an automated inspection system with bright field and dark field illumination. The detection of "macro-defects" such as scratches, incomplete photoresist coverage and non-uniform edge bead removal on a semiconductor wafer are detectable through the use of simultaneous bright and dark field illumination. Image data acquisition is achieved through illumination of an object by at least two light sources wherein light striking the patterned surface of a wafer respectively propagates dark and light field light paths which are collected by an imaging lens. Light sensitive sensors are positioned behind the lenses which concentrate the light passing through them on the light receiving surfaces of the sensors. Data captured by the light sensors is output in a form of digital data streams. The streams of digital data are processed for creation of a gray level deviation map from which an absolute difference image is used to detect bright field and dark field, defects. Although the above addresses nanometer topographical defects, subtleties of light degradation impede detection of transparent anomalies such as bones and parasites in translucent objects. Fish is not described for use in the method.

Japanese patent '534 A2 shows a device for inspecting defects. A binary image is formed using a light-field comparator by the instruction of the controller. Bright field illumination is removed and the roughed part of the object is inspected using only dark field illumination. Dark field illumination is removed and the plane part of an object is inspected using only light field illumination. This Japanese patent does not disclose a method of simultaneous detection of anomalies.

Japanese patent '222 A2 discusses a method for inspecting lenticular lens sheet.

The inspection apparatus reflects only dark field illumination to comprise the image using a "pickup means of" CCD line sensor cameras. Use of only dark field illumination impedes detection of anomalies only detectable by use of bright field illumination techniques.

Finally, an inspection device is disclosed in Japanese patent '637 A2. Use of a bright field lighting source or a dark field lighting source is selected according to the object being inspected, optionally both may be used.

The above references are known to improve the overall detection of distinguishing features and anomalies in objects, but none of the above art provides a solution for simultaneous detection of surface, embedded and semi-transparent edge anomalies.

The purpose of the invention is therefore to provide an automatic inspection apparatus and method for simultaneous detection of surface, embedded and semi-transparent edge anomalies in translucent objects.

SUMMARY OF THE INVENTION

It is therefore a feature of certain embodiments of the present invention to provide an automated imaging apparatus for detection of anomalies in 3D translucent objects.

In one embodiment, there is provided an automated inspection apparatus detection of anomalies in a 3D translucent object, the apparatus having a scanhead assembly including an image processing unit and image capture device, a first and a second light source, and conveyor means, a light block member positioned along a substantially common axis of the image capture device and a light source.

A further aspect of the present invention of the above embodiment is where the scanhead assembly has an image capture device, a computer processing unit in use with the image capture device to store and/or output scanned images and the assembly also includes an illumination member having illumination means which operates to illuminate the object being inspected as well as support means for moving an object in the desired direction and the light block member includes a signal isolation means.

In another preferred aspect of the above embodiment of the present invention the apparatus has the first and second light sources being comprised of bright and dark field, respectively, the conveyer is made of a translucent material having diffusion properties, the light block member is made of a material having selective light transfer properties, and the signal isolation means is video paint which can be positioned therein or thereon.

A particularly preferred aspect of the scanhead assembly is where it includes at least one reflection member and the object displacement for isolating the objects having anomalies includes the use of pneumatic ejector arms.

In another embodiment of a preferred aspect of the invention, there is provided a frame assembly, having object displacement means, a conveyor means, a scanhead assembly, and further includes a light block member, and a first and a second illumination member, whereby the light block member being positioned between an illumination member and the translucent object. The frame assembly mounts the scanhead assembly. Those skilled in the art will understand the varying positioning of the assembly (separate, or otherwise), the illumination members and the light block member are in a spaced apart relationship whereby the scanhead assembly, the light source and the light block member are positioned along a substantially common axis.

It is also an aspect of the above embodiment that the scanhead assembly has an illumination member, an image storage device, a computer processing unit, an image capture device and at least one mirror, whereby the image capture device is adapted to be used with the computer processing unit; the image capture device, the light member and the translucent object are positioned coaxially.

A further aspect of the above embodiment is where the apparatus includes the first and second light sources being comprised of bright and dark field, respectively, the conveyer is made of a translucent material having diffusion properties, the light block member is made of a material having selective light transfer properties, and the signal isolation means includes video paint which can be positioned therein or thereon, the isolation means for isolating objects with anomalies includes pneumatic ejector arms.

According to another aspect of the present invention, there is provided a method of simultaneously detecting surface, embedded and semi-transparent edge anomalies in 3D translucent objects, includes the steps of:

providing a translucent object;
providing an image capture means for recording or viewing scanned image of translucent object;
illuminating an object with spaced apart first and second illumination members together with light diffusion member;
providing a light block member positioned between the second illumination means and the translucent object;
aligning an image capture device, a light block member and a second illumination member along a substantially common axis; and, scanning a translucent object for anomalies with an image capture device to acquire data images for simultaneous detection of anomalies.

In preferred embodiments of the above invention, there is included the step of providing the images to an image processing unit for the detection of anomalies present on or within a translucent object. In a further desirable embodiment scanning a translucent object may be achieved while an object moves between the illumination members and an image capture device. Preferably, a translucent object is an edible foodstuff. Furthermore, it is desirable the above embodiment includes use during food manufacture.

The present invention will also find use in other fields for detecting anomalies. An example of additional fields would be meat processing, such as chicken, as well as other edible foods stuffs, such as fruits and legumes. Further fields for the invention may be used includes glass, plastics, foam and the like where defects and anomalies are to be detected.

A 3D translucent object, at least a portion of whose surface region is translucent or absorbs light is, for the purposes of the description used in the specification, is to be considered to be a translucent object, since some absorption or reflection would occur in such an object and would permit application of the methods and apparatus of this. invention. An example of such an object would be a fish fillet wherein light would be absorbed by embedded and semi-transparent edge anomalies (which may also reflect light) and reflected by surface anomalies. Such imperfections would allow for the detection of these anomalies according to this invention.

Reference to objects herein can therefore be understood to include any object falling within the foregoing, including but not limited to a fish fillet. Likewise, reference to fish or particular nomenclature thereof can be understood to refer to any object which might be sorted according to the method and apparatus of this invention.

BRIEF DESCRIPTION OF THE DRAWINGS

Having thus generally described the invention, reference will now be made to the accompanying drawings illustrating the preferred embodiments in which.

DETAILED DESCRIPTION OF THE PREFERRED EMBODIMENTS

Figure 1:
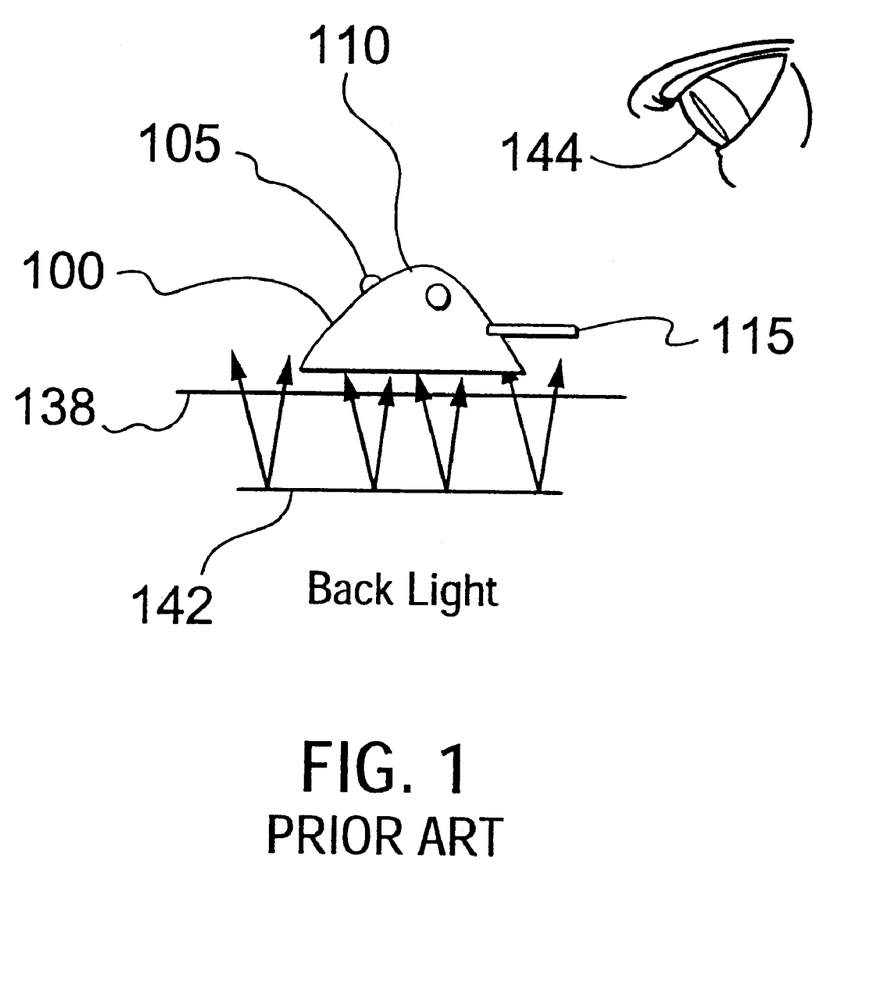
FIG. 1 is a schematic side-elevational view showing diagramatically a manual inspection operation according to Prior Art.

FIG. 1 illustrates a prior art, conventional imaging device, which is typical of the manual type of system used heretofore. In this system, an object to be scanned indicated by reference numeral 100 and which includes an embedded anomaly 110, a surface anomaly 105 and a semi-transparent edge anomaly 115 is placed manually on a transparent table 138. A source of light indicated by reference numeral 142 is provided as back light to illuminate the object 100 from beneath the table 138. An operator (indicated generally by reference numeral 144, visually scans the object 100 for anomalies. If the operator detects a surface anomaly 105 and a semi-transparent edge anomaly 115, the operator will either discard the object or put it aside for separate treatment. As explained previously, apart from human error, it is sometimes difficult to detect embedded anomalies 110 and consequently, an object with the embedded anomaly may erroneously be overlooked.

With reference to a typical apparatus according to the present invention as illustrated in FIGS. 2 through 6, there is provided an apparatus for the purposes of simultaneous detection of surface, embedded and semi-transparent edge anomalies in translucent objects. The apparatus is a two-lane embodiment where parallel rows of, e.g. fish fillets on a conveying system, are to be inspected. It will be understood that either single lane or three or more lanes can be used by modifying the apparatus of the present invention.

Figure 2:
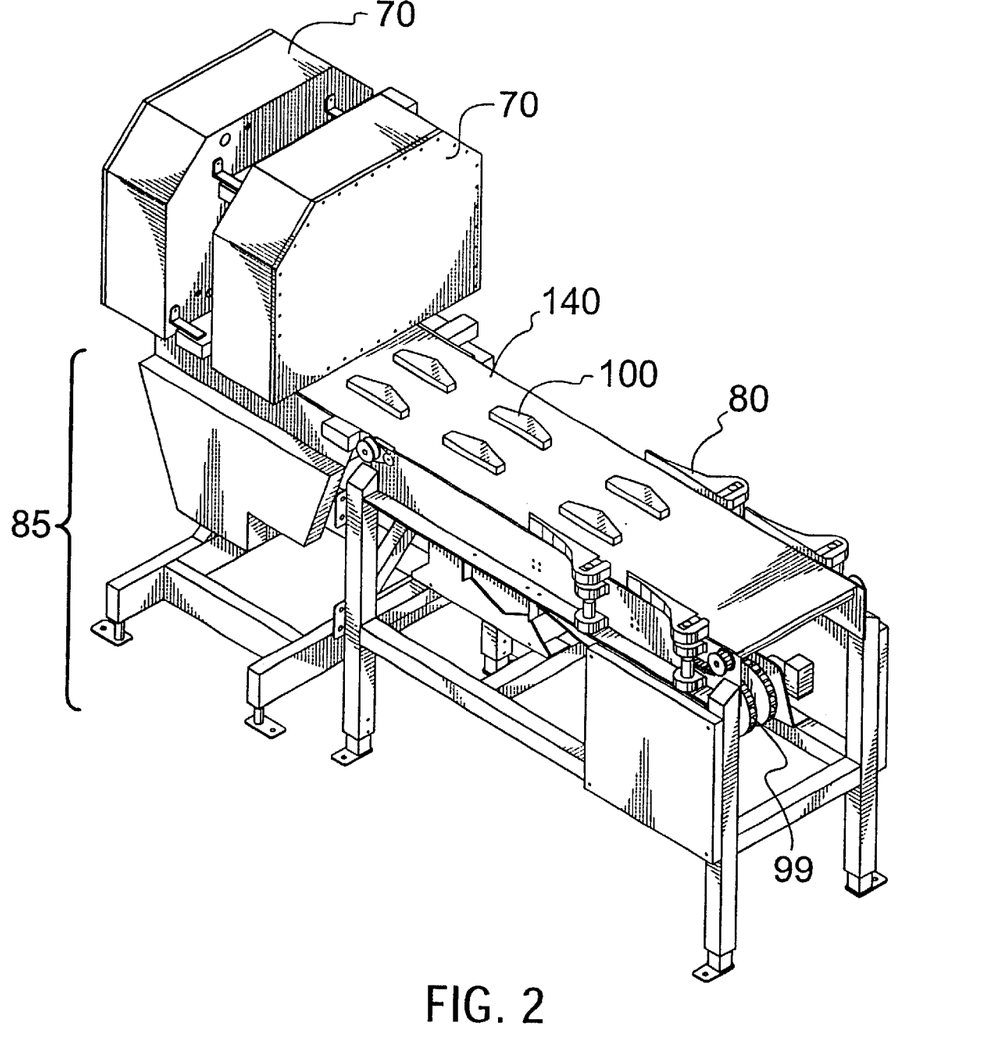
FIG. 2 is an perspective-elevational view, showing an apparatus of one embodiment of the present invention.

Referring to FIG. 2, the inspection apparatus includes a support frame 85, a movable surface, such as a conveyor belt 140 made of a light diffusing material for diffusing light from the second illumination member 40 and for movement of a fish fillet from a loading station (not shown) to and through a detection step and finally to a discharge station.

Suitable conventional means are provided for driving the conveyor belt, preferably the belt is an endless belt and with the belt continuously moving between loading station and discharge station (not shown).

To this end, the fish fillet is preferably transported by the conveyor 140 at a constant velocity, using a conventional servo-mechanism controlled by a suitable motor 99. The object to be scanned thus travels in a direction along a fixed scan axis further described herein. A scanhead assembly, indicated generally by reference numeral 70, is mounted by suitable means above the conveyor 140 in a fixed relationship thereto.

Figure 3:
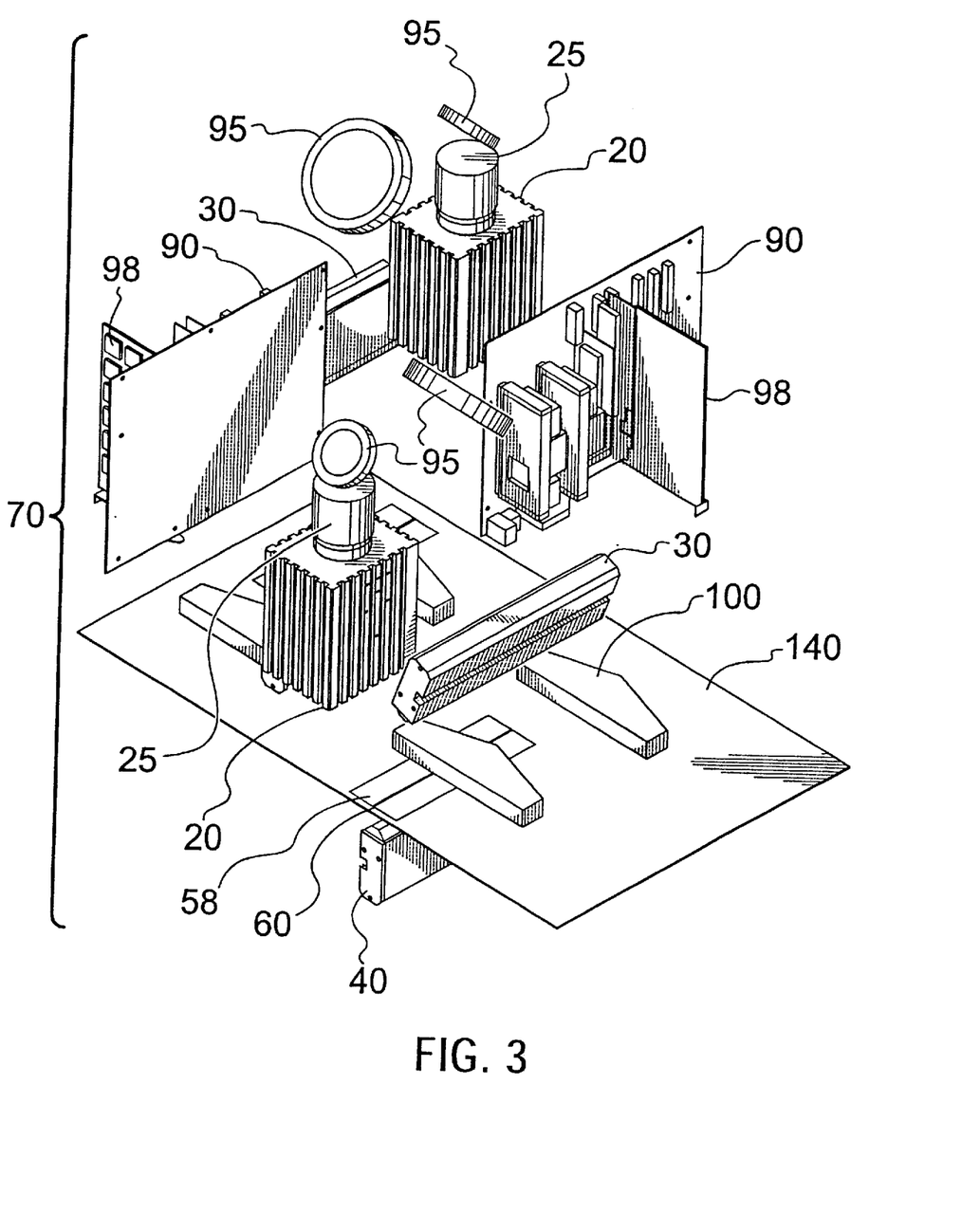
FIG. 3 is an exploded perspective-elevational view showing the interior of the scanhead assembly of FIG. 2.

With reference to FIG. 3 the scanhead assembly 70 includes a camera 20, a computer processing unit 90, and a frame grabbing device 98 for grabbing or storing the images. The scanhead assembly may also include the first illumination member 30 and reflection members 95, such as mirrors. This embodiment may be employed to reduce the overall height of the scanhead assembly 70 but, obviously, if height is not a factor, such reflecting members need not be employed.

The apparatus of the present invention may include pneumatic ejection means for removing objects 100 having surface 105, embedded 110, or transparent edge 115 anomalies from the conveyor belt 140. Such ejection means may be in the form of movable arms actuated in response to the detection of an anomaly by the scanhead assembly so that the objects are removed either for further processing or to be discarded. The structure of the ejector arms 80 and their operating mechanism is known per se in different fields and consequently, they will not be described in further detail.

It will be seen from FIG. 3, that the apparatus includes an image capture device 20 (or camera), a first illumination member (or front illumination member) 30, a second illumination member which is lamp 40, a light block member 50 having selected light transfer properties, one being a signal isolation means 60, a computer processing unit 90, image storage device 98, a conveyor belt 140 for light diffusion and movement of a translucent object 100. The light block member 50 will be described hereinafter in greater detail with reference to FIG. 6. In general, the light block member includes a signal isolation component with an impermeable barrier or stripe position thereon which the line scan camera 20 is focused thereon. In one embodiment, the barrier or stripe can be in the form of a light impermeable layer formed by use of a coating known as Ultimatte Super Blue (TM) video. paint as the signal isolation means.

As illustrated in FIG. 3, the camera 20 includes a lens 25 for detection and a scanning of the translucent object 100 for any anomalies. Detection of these anomalies, designated by reference numerals 105, 110, and 115, involves illumination of the translucent object 100. As an object 100 moves into the scan area, shown as a line of sight from the lens (being indicated by reference numeral 25 and shown as a dotted line in FIG. 5), and the signal isolation component 58, the camera records a signal, which is processed as described hereinafter. In this arrangement, light from light source 30 strikes the object 100 and in turn is received by the sensors of the line scan camera.

In a preferred embodiment, the scanning involves a continuous or sequential two dimensional array technique providing a two dimensional graphic image of an object. Bright field image data and dark field image data are simultaneously captured by a single imaging device. The output data from the imaging device is fed to a computer processing unit.

A central processing unit (CPU) can be any conventional type and is known in the art. The scanned image is then processed by the computer processing unit 90 which is conventional and is the same as those used in the art. For this reason, portions of the computer processing unit 90 will not be discussed in further detail other than to describe the operation of the unit. The illumination energy is of sufficient intensity to maintain the image capture speed and minimum image blur requirements.

Figure 4:
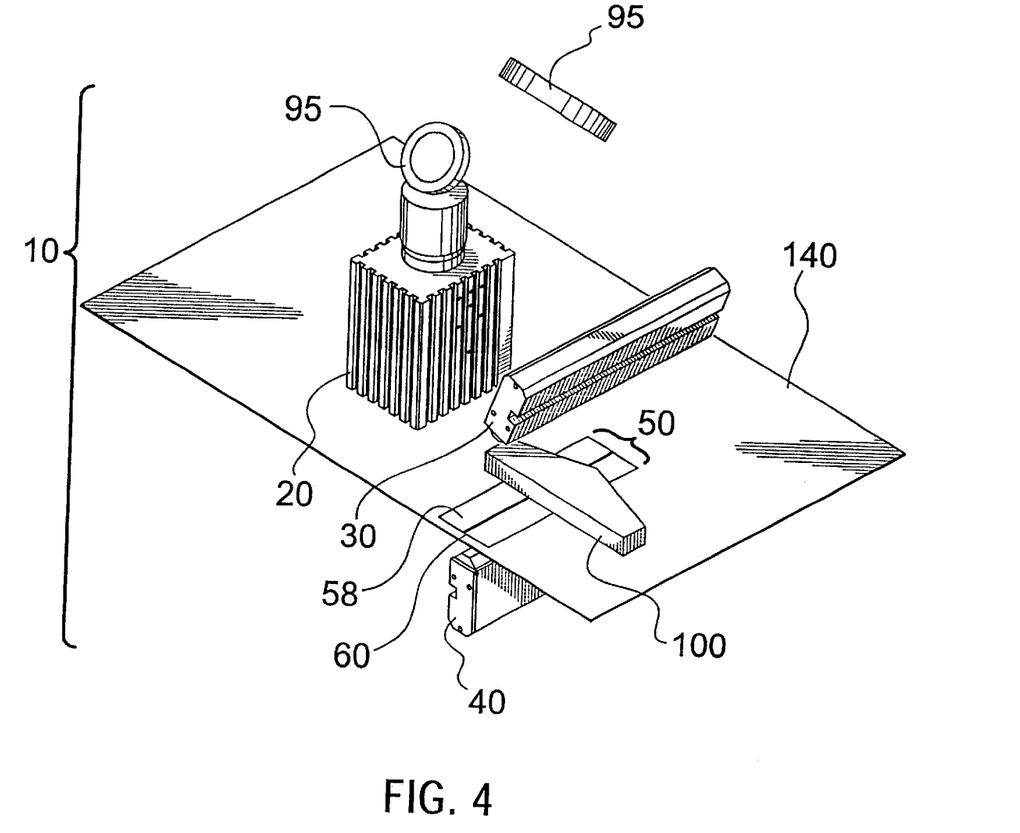
FIG. 4 is a perspective-elevational view of a portion of the scanhead assembly of FIG. 3.
Figure 5:
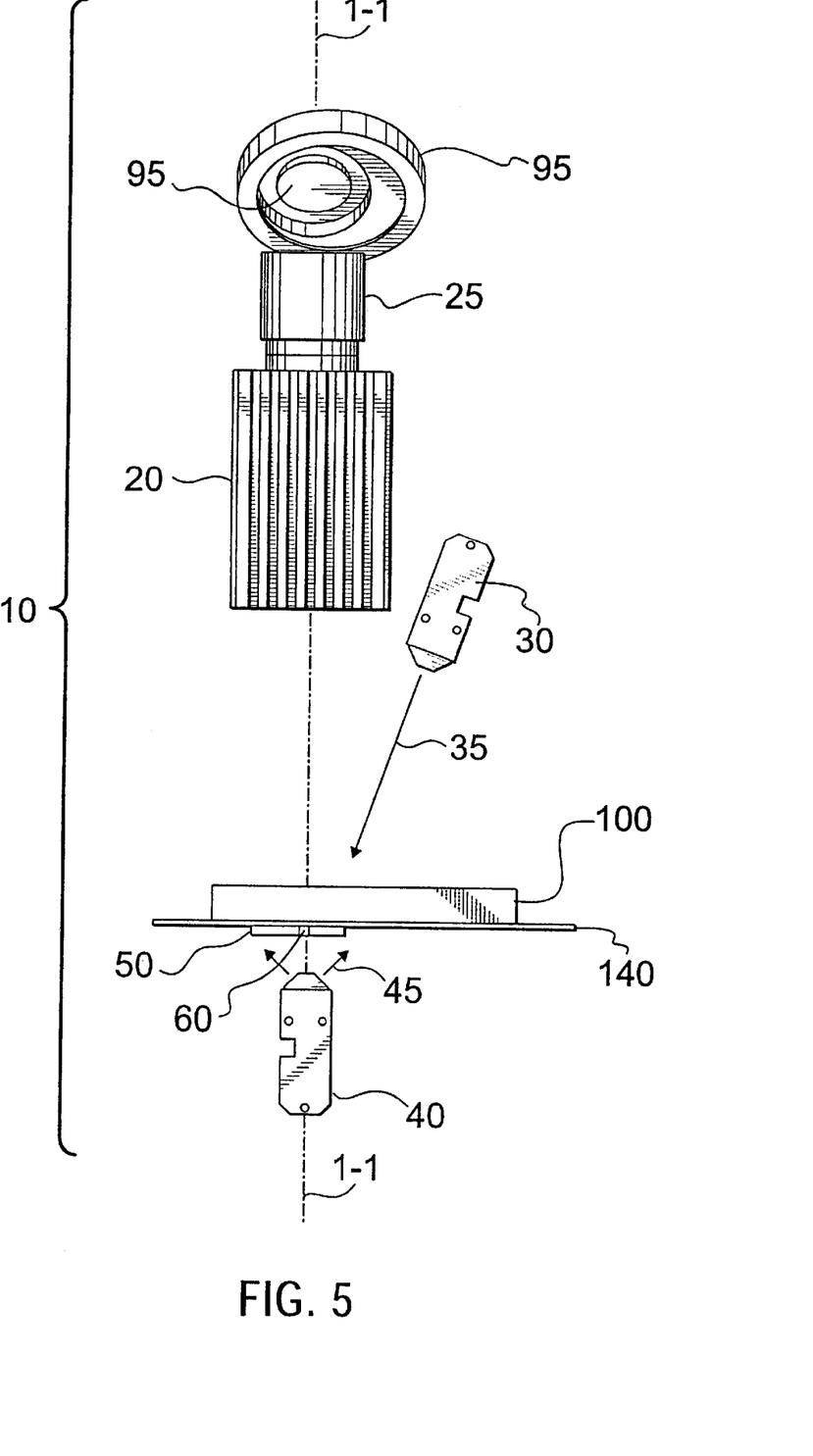
FIG. 5 is an side elevation view of the apparatus of FIG. 4, illustrating in greater detail various components.

FIGS. 4 and 5 show the first illumination member 30, in a preferred embodiment, providing a Bright Field frontal lighting means 35 (FIG. 5) and the second illumination member 40 providing Dark Field back lighting means 45 (FIG. 5). The lamp 40 is positioned in coaxial alignment with the camera 20 (illustrated by a broken line 1—1 in FIG. 5). The front illumination member 30 is positioned at an oblique angle relative to the surface of an object to be scanned to provide bright field light paths that strike the surface of the object. The front illumination source 30 can be mounted in different positions although, as illustrated in FIG. 5 a preferred position is at an oblique angle to the object to be scanned and to the light block member 50. The reason for this is simply for limiting the size of the apparatus. Other coaxial arrangements may be employed, so long as the camera 20 does not directly tee the light emitted from the lamp 30.

Skilled persons in the art will appreciate that conventional lamp configurations such as halogen lamp tubes and the like may be used for illumination of an object. Other lamp sources such as light beams formed by LED's or laser beams may also be used and achieved by a string of point sources positioned in optical association with a light diffusing element. Thus, any suitable type of illumination can be employed for this invention within the Ultra Violet to IR light spectrum. Preferred light sources are fiber optic line array devices for each member 30 and 40.

Figure 6:
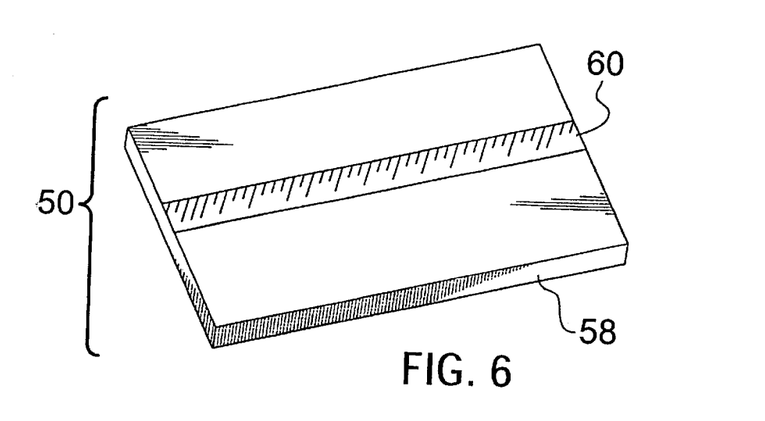
FIG. 6 is an enlarged view of light block member used in the apparatus of the present invention.

The light block member 50, illustrated in FIG. 6, includes a block support member being a solid transparent material. The size of the light block member 50 in terms of the physical dimensions of the signal isolation means 60 will vary depending on the light source and/or imaging lens magnification. In other words, the width of the signal isolation component 60 will vary depending on the capability of the line scan camera 20, it being understood that normally this isolation strip will be relatively narrow when the camera 20 is scanning a relatively narrow area.

The block member 50 is preferably formed from an illumination pervious or transparent material 58 such as glass, optically clear plastic or some other such suitable material. The transparency of this material may vary depending on the type of system used and the degree of illumination required by the back lighting.

The signal isolation means 60 is positioned on or in the light block member 50 (as desired for optimum manufacturing assembly). Desirably, it is positioned coaxially with the lamp 40 and the camera 20. For the purposes of sanitation for food inspection the light block member is protectively encapsulated by a thin plastic material or the like which allows the light block to function in a similar manner.

The camera 20, as shown in FIGS. 3 through 5, may be a conventional camera such as a line scan camera or other suitable known image capture device, and is aligned axially (illustrated by a broken line 1—1, in FIG. 5) with a lamp 30 and/or 40, the light block member 50 and the translucent object 100. In the preferred embodiment; the light block member is positioned between a conveyor belt 140 and the lamp 40. The conveyor belt 140 acts as a light diffusing member wherein the light block member 50, provides for the simultaneous detection of surface 105, embedded 110 and semi-transparent edge 115 anomalies in translucent objects 100.

As illustrated in FIG. 6, the light block 50 includes a signal isolation means 60 positioned therein or thereon. The signal isolation means 60 is preferably video paint and corresponds to the operational characteristics of the camera 20. In use the signal isolation means 60 blocks, or otherwise obstructs, the light emitted from the lamp 40 such that the camera 20 does not detect direct light and overexposure of the scanned image is prevented. The light block supporting member 58 is preferably made of an illumination pervious material, such as glass, which allows the light from the lamp 40 to be distributed evenly on remaining portions of the translucent object 100 during scanning.

Effective blocking of the light from the direct perspective of the camera 20 enables the reliable detection of surface anomalies 105 with frontal lighting 30. It will be understood that other means of forming the light block can be employed such as thin bands of tape suitably secured to or mounted in the light block supporting member 58.

Similarly, overall detection of surface 105, embedded 110 and semi-transparent edge 115 anomalies is improved due to the position of the light block member 50 since increased illumination values will not saturate the camera 20.

It is desirable at times to eliminate ambient light from the inspection area of the object 100. For example, extreme brightness from ambient light sources will result in "stray" light being directed at the object 100, forming shadows and the like, which prevent proper illumination of the object 100. Thus, use of a shroud (not shown) allows for controlled conditions during inspection of the object 100. Although use of a shroud (not shown) is an embodiment of the invention it is not limiting to use of the present invention.

It is therefore evident from this disclosure that defects or anomalies associated with inspection of a translucent object 100 can be simultaneously detected by use of the present invention 10. The present invention 10 enables the simultaneous detection of surface anomalies 105 (white skin, black skin, scales, fins with skin, melanin spots, etc.) embedded anomalies 110 (parasites, blood, bruises, soars) and semitransparent edge anomalies 115 (bones without skin) to be detected in the translucent objects (e.g. fish).

A primary advantage of the invention is that it is capable of automatically and concurrently identifying and processing distinguishing features or anomalies, the characteristic signatures of which are revealed by either one or a combination of bright field illumination and dark field illumination. The invention detects the presence of any such distinguishing features or anomalies and is especially useful during inspection of 3D translucent objects, such as a fish fillet.

The preferred embodiment described herein shows the inspection apparatus in use after a fish has been processed (i.e. entrails removed). However, the inspection apparatus can be used before or after any process step at any stage of preparation of a fish fillet.

Those skilled in the art to which the invention pertains understand the invention has been described by way of a detailed description of a preferred embodiment and departures from and variations to this arrangement may be made without departing from the spirit and scope of the invention, as the same is set out and characterized in the accompanying claims.

We claim:

1. In an automated inspection apparatus for detection of anomalies in a 3D translucent object, said apparatus having a scanhead assembly including an image processing unit and image capture device, a first front light source, a second back light source and a conveyor means, the improvement comprising: a light block member having a solid continuous light isolation means, said light block member positioned along a substantially common axis of said image capture device and one of said light sources wherein said light block member substantially prevents direct light transmission of said one light source to said image capture device.

2. The automated inspection apparatus as defined in claim 1, wherein said scanhead assembly comprises:

a computer processing unit for use with said image capture device to store and/or output scanned images;

and wherein said assembly further includes said first and second light sources comprising bright field illumination and dark field illumination, operative to illuminate said object; and wherein said conveyor means is a support means adapted to move an object in the desired direction.

3. The automated inspection apparatus according to claim 2, wherein said bright field illumination is adapted to detect surface anomalies and said dark field illumination is adapted to detect embedded and semi-transparent edge anomalies.

4. The automated inspection apparatus according to claim 2, wherein said image capture device is a one dimensional line scan camera.

5. An automated inspection apparatus according to claim 1, wherein said conveyer means comprises a translucent material having diffusion properties.

6. The automated inspection apparatus of claim 1, wherein said light block member is made of a material having selective light transfer properties.

7. The automated inspection apparatus of claim 1, wherein said scanhead assembly further comprises at least one reflection member.

8. The automated inspection apparatus according to claim 1, wherein said apparatus includes means, having pneumatic ejector arms, for isolating objects with anomalies.

9. In an automated inspection apparatus for detection of anomalies in a 3D translucent object including a frame assembly having object displacement means, conveyor means for conveying said object, and a scanhead assembly, the improvement comprising:

a light block member having a solid continuous light isolation means;

a first front light source and a second back light source;

said light block member being positioned between one of said light source and said translucent object;

said frame assembly operatively associated with said scanhead assembly;

said one light source and said light block member being in spaced apart relationship whereby said scanhead assembly, said one light source and said light block member are positioned along a substantially common axis, said scanhead assembly adapted to simultaneously detect surface anomalies, embedded anomalies and semi-transparent edge anomalies in an object.

10. The automated inspection apparatus of claim 9, wherein said scanhead assembly comprises said first and second light source lighting said translucent object with dark and bright field illumination, an image storage device, a computer processing unit, an image capture device and at least one mirror.

11. The automated inspection apparatus of claim 9, wherein said apparatus comprises:

a computer processing unit;

an image capture device adapted to be used with said computer processing unit;

said image capture device, at least one of said first and second light source, said light block member and said translucent object are positioned coaxially.

12. An automated inspection apparatus according to claim 9, wherein said first and second light sources comprises bright and dark field respectively.

13. An automated inspection apparatus according to claim 9, wherein said conveyer means comprises a translucent material having diffusion properties.

14. The automated inspection apparatus of claim 9, wherein said light block member is made of materials having selected light transfer properties.

15. The automated inspection apparatus according to claim 9, wherein said apparatus includes means, having pneumatic ejector arms, for isolating objects with anomalies.

16. The automated inspection apparatus of claim 9, wherein said first light source illuminates said translucent object with bright light and said second light source illuminates said translucent object with dark light.

17. A method of simultaneously detecting surface, embedded and semi-transparent edge anomalies in a 3D translucent object comprising the steps of:

providing a translucent object;

illuminating said object with spaced-apart first front light and second back light source;

positioning a light block member having a solid continuous isolation means between at least one of said light source and said translucent object;

aligning an image capture device, said light block member, and said at least one light source along a substantially common axis;

scanning said translucent object for recording or viewing a scanned image of said object with said image capture device; and identifying simultaneously surface anomalies, embedded anomalies, and semi-transparent edge anomalies in said object.

18. A method according to claim 17, wherein scanning said translucent object takes place while said object moves between said illumination members and said image capture device.

19. A method according to claim 17, wherein said translucent object is an edible foodstuff.

20. A method as defined in claim 17, wherein said image capture device is used during fish processing.

21. The method according to claim 17, wherein said first and second light source have bright field illumination and dark field illumination, respectively.

* * * * *